United States Patent
Keyzer et al.

(10) Patent No.: US 9,985,290 B2
(45) Date of Patent: May 29, 2018

(54) MAGNESIUM SALTS

(71) Applicant: Dyson Technology Limited, Wiltshire (GB)

(72) Inventors: Evan Keyzer, Cambridge (GB); Clare Grey, Cambridge (GB); Hugh Glass, Cambridge (GB); Dominic Wright, Cambridge (GB)

(73) Assignee: Dyson Technology Limited, Malmesbury, Wiltshire (GB)

( * ) Notice: Subject to any disclaimer, the term of this patent is extended or adjusted under 35 U.S.C. 154(b) by 341 days.

(21) Appl. No.: 15/043,888

(22) Filed: Feb. 15, 2016

(65) Prior Publication Data

US 2017/0237072 A1    Aug. 17, 2017

(51) Int. Cl.
*H01M 6/16* (2006.01)
*H01M 4/60* (2006.01)
(Continued)

(52) U.S. Cl.
CPC ............. *H01M 4/60* (2013.01); *C07C 253/30* (2013.01); *C07C 255/03* (2013.01);
(Continued)

(58) Field of Classification Search
CPC .... H01M 4/60; H01M 10/056; H01M 10/054; H01M 6/162; H01M 6/183;
(Continued)

(56) References Cited

U.S. PATENT DOCUMENTS

2012/0141889 A1* 6/2012 Lee .................. H01M 12/06
429/405
2013/0196206 A1* 8/2013 Park .................. H01M 8/20
429/101
(Continued)

FOREIGN PATENT DOCUMENTS

| EP | 0 407 121 | 1/1991 |
|---|---|---|
| JP | 2015-106467 | 6/2015 |
| JP | 2015-115233 | 6/2015 |

OTHER PUBLICATIONS

Ha, S.Y. et al. (2014). "Magnesium(II) Bis(trifluoromethane sulfonyl) Imide-Based Eletrolytes with Wide Electrochemical Windows for Rechargeable Magnesium Batteries," *ACS Applied Materials & Interfaces* 6(6): 4063-4073.
(Continued)

*Primary Examiner* — Stewart A Fraser
(74) *Attorney, Agent, or Firm* — Morrison & Foerster LLP

(57) ABSTRACT

Described is a salt of the general formula: $Mg^{2+}(L_x)_6(PF_6)_2$ wherein each L is a ligand selected from dichloromethane, a cyclic ether, or a nitrile of the general formula $R-C\equiv N$. The method of making the salt comprises the steps: providing Mg metal, activating the Mg metal in a first dry solution comprising a first ligand solution ($L_1$), treating the dry solution of activated Mg metal and $L_1$ with $NOPF_6$ in a second dry solution comprising a second ligand solution ($L_2$), heating the treated Mg metal solution removing residual solvent under vacuum, and recrystallizing the
(Continued)

remaining solid to form the salt wherein $L_x$ comprises a mixture of $L_1$ and $L_2$. The salt can be used as the salt in an electrolyte, or as an additive to an electrolyte, in a cell or battery.

19 Claims, 8 Drawing Sheets

(51) Int. Cl.
    *C07C 253/30*      (2006.01)
    *C07C 255/03*      (2006.01)
    *H01M 6/18*      (2006.01)
    *H01M 10/054*      (2010.01)
    *H01M 10/056*      (2010.01)

(52) U.S. Cl.
    CPC ........... *H01M 6/162* (2013.01); *H01M 6/183* (2013.01); *H01M 10/054* (2013.01); *H01M 10/056* (2013.01); *H01M 2300/0025* (2013.01); *H01M 2300/0065* (2013.01)

(58) Field of Classification Search
    CPC .. H01M 2300/0025; H01M 2300/0065; C07C 255/03; C07C 253/30
    See application file for complete search history.

(56) References Cited

U.S. PATENT DOCUMENTS

2014/0127594 A1* 5/2014 Nakayama ............. G01N 27/26
                                                                                                     429/403
2016/0308248 A1* 10/2016 Burrell ............. H01M 10/0569

OTHER PUBLICATIONS

Keyzer, E.N. et al. (2016). "$Mg(PF_6)_2$-Based Electrolyte Systems: Understanding Electrolyte-Electrode Interactions for the Development of Mg-Ion Batteries," *Journal of the American Chemical Society* 138: 8682-8685.

Veryasov, G. et al. (Jan. 2016). "Homoleptic octahedral coordination of $CH_3CN$ to $Mg^2$ in the $Mg[N(SO_2CF_3)_2]_2$—$CH_3CN$ system," *Dalton Transactions* 45:2810-2813.

Royal Society of Chemistry. "RSC Main Group Chemistry Group Annual Meeting and AGM," Handout. Sep. 11, 2015, Burlington House, London; 37 pages.

Royal Society of Chemistry. "Dalton Younger Members Event," Handout. Sep. 9-10, 2015, University of Leeds, Leeds, United Kingdom; 24 pages.

Keyzer et al. "Hexafluorophosphate Salts of Mg and Ca," Poster session presented at the Dalton Younger Members Event. Sep. 9-10, 2015, University of Leeds, Leeds, United Kingdom; 1 page.

* cited by examiner

MAGNESIUM SALTS

FIELD OF THE INVENTION

The present invention relates to a salt of magnesium hexafluorophosphate. Additionally, the present invention relates to a method of making a magnesium hexafluorophosphate salt and the use of the magnesium hexafluorophosphate salt as an electrolyte in a cell or battery.

BACKGROUND OF THE INVENTION

Lithium-ion batteries are currently used in a variety of electronic devices. The use of lithium-ion cells has prevailed over other battery technologies due to the ability of a lithium-ion cell to be recharged without a loss of a significant charge capacity in the short term. In addition, the energy density of a lithium-ion battery enables its use in portable products such as laptop computers and mobile phones. Over time however, lithium batteries are known to suffer from loss of charge capacity. Furthermore, issues of thermal runaway and overheating risks have been widely reported.

Many lithium-ion electrolyte systems have been developed and studied using a wide range of lithium salts including $LiBF_4$, $LiClO_4$, $LiNTF_2$, $LiPF_6$, $LiAsF_6$, and $LiSbF_6$ as well as others. $LiPF_6$ is the preferred electrolyte in lithium-ion cells due to its balance of several properties that no other lithium salt has been found to possess. However, there are concerns over the long term use of lithium cells, given the relatively low abundance of lithium in the Earth's crust and the current high price of lithium relative to other Alkali and Alkaline Earth metals.

SUMMARY OF THE INVENTION

In a first aspect, the present invention provides a salt of the general formula:

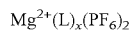
$$Mg^{2+}(L)_x(PF_6)_2 \quad (i)$$

wherein x represent a number between 1 and 6 and each L represents a ligand selected from one of the following compounds: a halomethane, a cyclic crown ether, or a nitrile of the general formula R—C≡N.

It has been recognised theoretically that alkaline earth metals such as magnesium could be used as electrolyte solutions in electrochemical cells and batteries. Magnesium is both highly abundant in the Earth's crust and therefore less expensive per ton than other Alkali and Alkaline Earth metals. In addition, magnesium has a higher charge capacity than lithium. Furthermore, in a magnesium-ion cell, magnesium metal can be used as the metal anode without the risk of thermal runaway due to dendrites not forming on the magnesium metal. However, despite this knowledge magnesium has not been widely adopted as an electrolyte or as a material for anodes because of difficulties in forming electrolytes that are stable over a wide voltage range and also compatible with multiple electrodes.

As mentioned above, the lithium hexafluorophosphate salt is the preferred electrolyte in lithium-ion cells. However, a barrier for using a magnesium hexafluorophosphate based electrolyte in magnesium-ion batteries is the fact that the synthesis of an Alkaline Earth metal hexafluorophosphate salt can be costly and more problematic (often resulting in lower purity materials) when compared with the synthesis of a lithium hexafluorophosphate salt. Furthermore, the $PF_6^-$ anion in $MgPF_6$ is claimed to react with magnesium metal anodes, forming layers of passivating $MgF_2$. It has been found however that the magnesium hexafluorophosphate salt of the present invention can be readily synthesised in solution at relatively mild conditions, and also that the resulting salt can be used as an electrolyte in coin cell batteries without passivation occurring at the anode.

The term salt used throughout the specification is intended to cover complex magnesium salts with ligands (L) that fall within the general formula given above. The choice of ligand or mixture of ligands may allow for a more stable reaction mixture in the synthesis of the magnesium hexafluorophosphate salt. When x is greater than one, each ligand may be independently selected from a halomethane, or a cyclic crown ether or a nitrile compound. With a view to simplifying the reaction mixture during synthesis, when x is greater than 1, L may represent a ligand selected from one only of the following compounds: a halomethane, a cyclic crown ether, or a nitrile of the general formula R—C≡N. That is to say that L may comprise two or more halomethanes, cyclic crown ethers, or two or more nitriles of the general formula R—C≡N.

The halomethane may be a chlorinated methane, such as $CH_2Cl_2$, $CHCl_3$, $CCl_4$. The chloromethanes represent stable and cost effective dry solvents for the synthesis. Dichloromethane ($CH_2Cl_2$) is particularly suited as a ligand and solvent for the synthesis of the magnesium salt due to its low boiling point and solvating characteristics.

The cyclic crown ether can comprise typical cyclic crown ethers selected from one of the following: [12]-crown-4, [18]-crown-6, [24]-crown-8. The cyclic crown ether may be used to sequester the magnesium cation. The use of a multidentate ligand can be favourable since the magnesium cation remains in solution but has a lowered reactivity and could also inhibit the plating of magnesium onto an electrode surface. These cyclic crown polyethers can be used in combination with halomethane based solvents such as $CH_2Cl_2$, $CHCl_3$, $CCl_4$, without hindering the desired synthesis of the magnesium salt.

In terms of the general formula for the nitrile, and when x is equal to 6, each R may represent an organic group independently selected from the following: methyl, ethyl, propyl, butyl, ᵗbutyl, pentyl, ethylene, propylene, butylene, pentylene, toluene, naphthalene, or phenyl. A sterically bulky ligand could prevent the solvation of the magnesium cation. Therefore for the general formula, R may preferably represents a group that would provide a nitrile that is considered to have low sterically hindrance.

Each L may be the same nitrile. This renders the synthesis of the salt more straightforward since the same nitrile solution can be used in both the activation and the treatment steps. For the salt, L may be acetonitrile, which is the least sterically hindered nitrile. As an added advantage, the use of acetonitrile provides good solvation of the magnesium cation, as well as low manufacturing expense since desolvation under high vacuum can be more easily achieved than with other solvents. This desolvated salt could then be re-solvated with, for instance, an ether (such as THF, diethyl ether) or another donor solvent.

In a second aspect, the present invention provides a method of making a salt of the general formula:

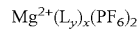
$$Mg^{2+}(L_y)_x(PF_6)_2 \quad (ii)$$

wherein x represent a number between 1 and 6, $L_y$ represents a ligand independently selected from any one of the following compounds: a halomethane, a cyclic crown ether, or a nitrile of the general formula R—C≡N, and $L_y$ comprises a mixture of compounds $L_1$ and $L_2$, the method comprising:

providing Mg metal, washing and activating the Mg metal in a first dry solution comprising a first compound ($L_1$), treating the solution of activated Mg metal and first compound $L_1$ with $NOPF_6$ in a second dry solution comprising a second compound ($L_2$), removing the residual solvent, and recrystallizing the remaining solid to form the salt of Formula (ii).

The residual solvent can be removed by evaporation, for example, under vacuum or by heating.

In a third aspect, the present invention provides an electrolyte comprising a salt in accordance with the above Formula (i) or Formula (ii). The electrolyte may comprise the salt as an additive to a conventional electrolyte, or the salt may be used in a pure solution to form, with an appropriate solvent, an electrolyte by itself.

In a fourth aspect, the present invention provides a cell or battery comprising an electrolyte in accordance with the above Formula (i) or Formula (ii). The salts of the present invention do not suffer from some of the same disadvantages observed with the use of lithium salts in electrochemical cells or batteries. In addition, the salts of the present invention can be used in electrolytes in a number of cell or battery systems. More specifically, the cell or battery can be, for example, a lithium cell or a lithium-ion cell. However, the cell or battery using the salts of the present invention may be more generally described as a metal based, or a metal-ion based cell or battery. Examples of other metal or metal-ion based cells or batteries may include magnesium, calcium or aluminium metals or ions. When using the salt of the present invention in an electrolyte in metal cell or battery, metals such as magnesium, calcium or aluminum may be used as the metal anode without the risk of the salt decomposing. Another advantage is that the salt of the present invention may be useful in terms of reducing or limiting the corrosion of aluminum current collectors used in metal or metal-ion based cells or batteries.

BRIEF DESCRIPTION OF THE DRAWINGS

In order that the present invention may be more readily understood, an embodiment of the invention will now be described, by way of example, with reference to the accompanying Figures, in which.

DETAILED DESCRIPTION OF THE INVENTION

The present invention will now be illustrated with reference to the following examples.

EXAMPLE 1

Synthesis of $Mg(CH_3CN)_6(PF_6)_2$

Magnesium metal in the form of Magnesium powder (>99%) from Sigma Aldrich was washed and activated with approximately 10 mg of $I_2$ until the solution became colourless. The resulting mixture was solvated dropwise in dry solution of $CH_3CN$ and $NOPF_6$ (purchased from ACROS Organics) under an atmosphere of dry $N_2$ at room temperature. After adding the $NOPF_6$ solution, the reaction mixture evolved a colourless gas (NO) which was vented from the reaction flask under dry $N_2$. The solution was heated gently to 45° C. overnight. The equation for the reaction is given below (1).

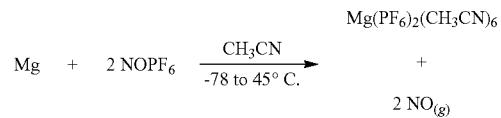

After removal of solvent, an off-white solid was recrystallized twice from hot acetonitrile, affording a white crystalline powder of $Mg(CH_3CN)_6(PF_6)_2$ with a yield of 52%.

EXAMPLE 2

Characterisation of $Mg(CH_3CN)_6(PF_6)_2$

Figure 1:
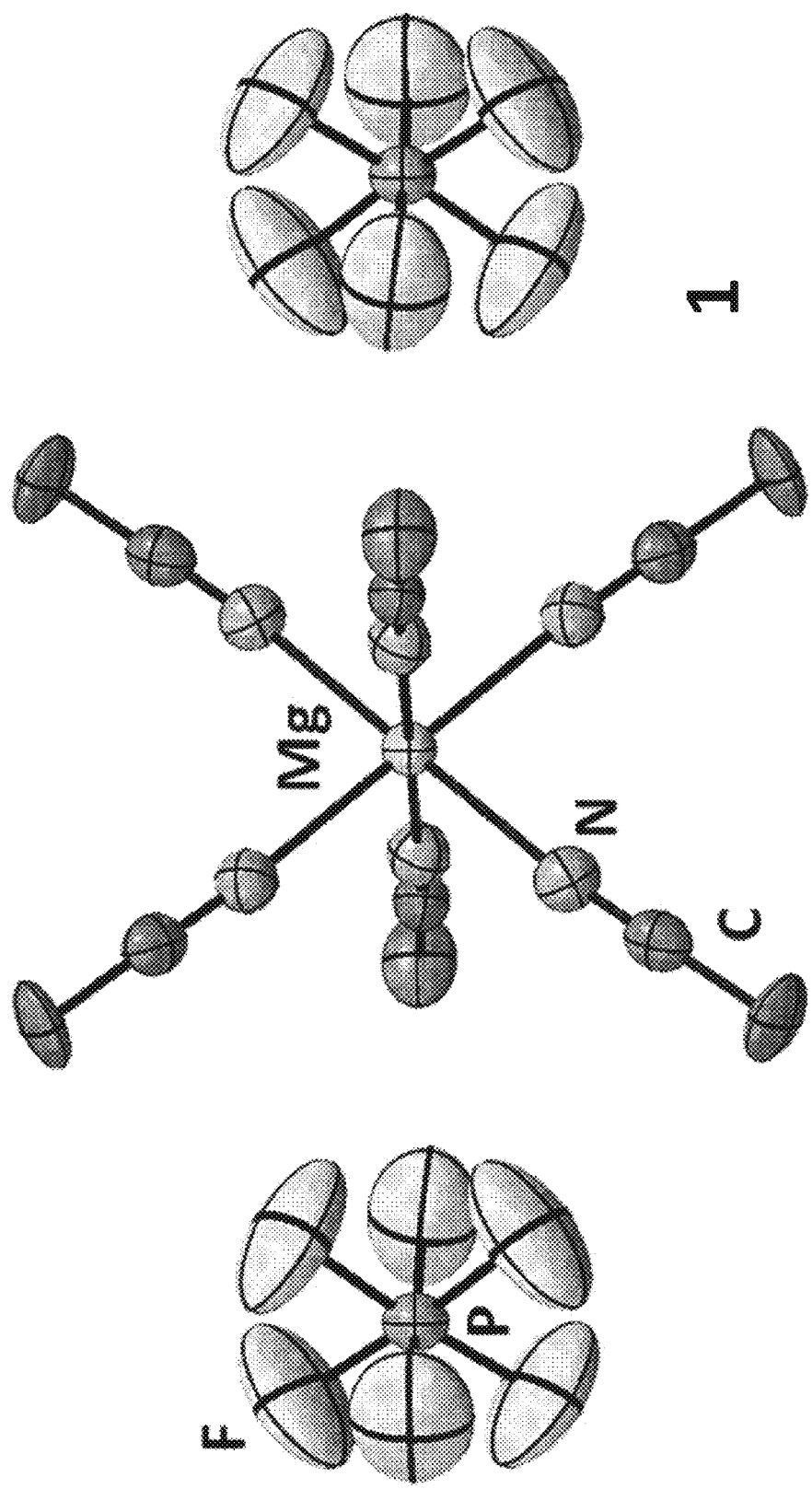
FIG. 1 is an X-ray crystal structure of a salt of the present invention.
Figure 2:
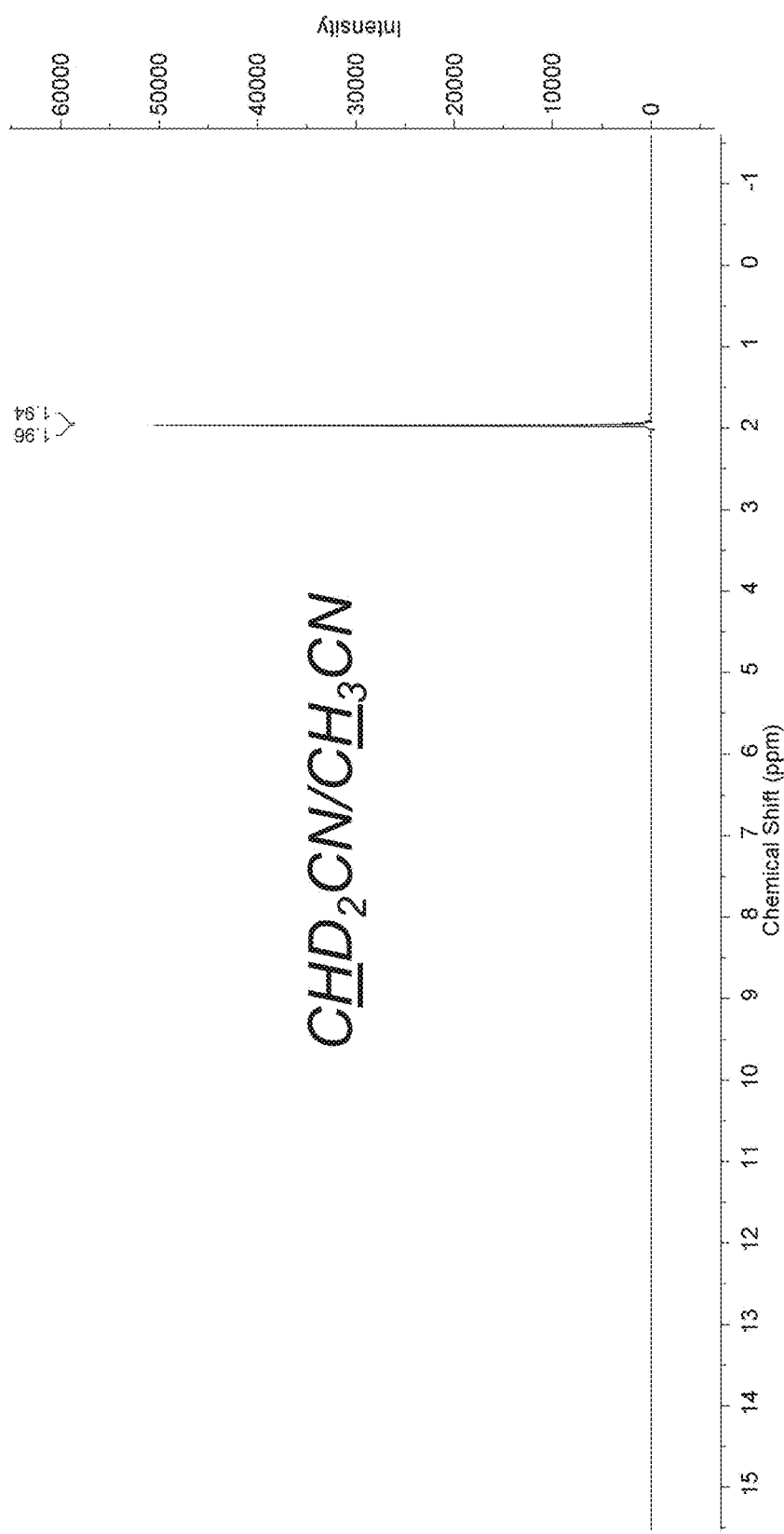
FIG. 2 is a $^1H$ NMR spectrum of a salt of the present invention.
Figure 3:
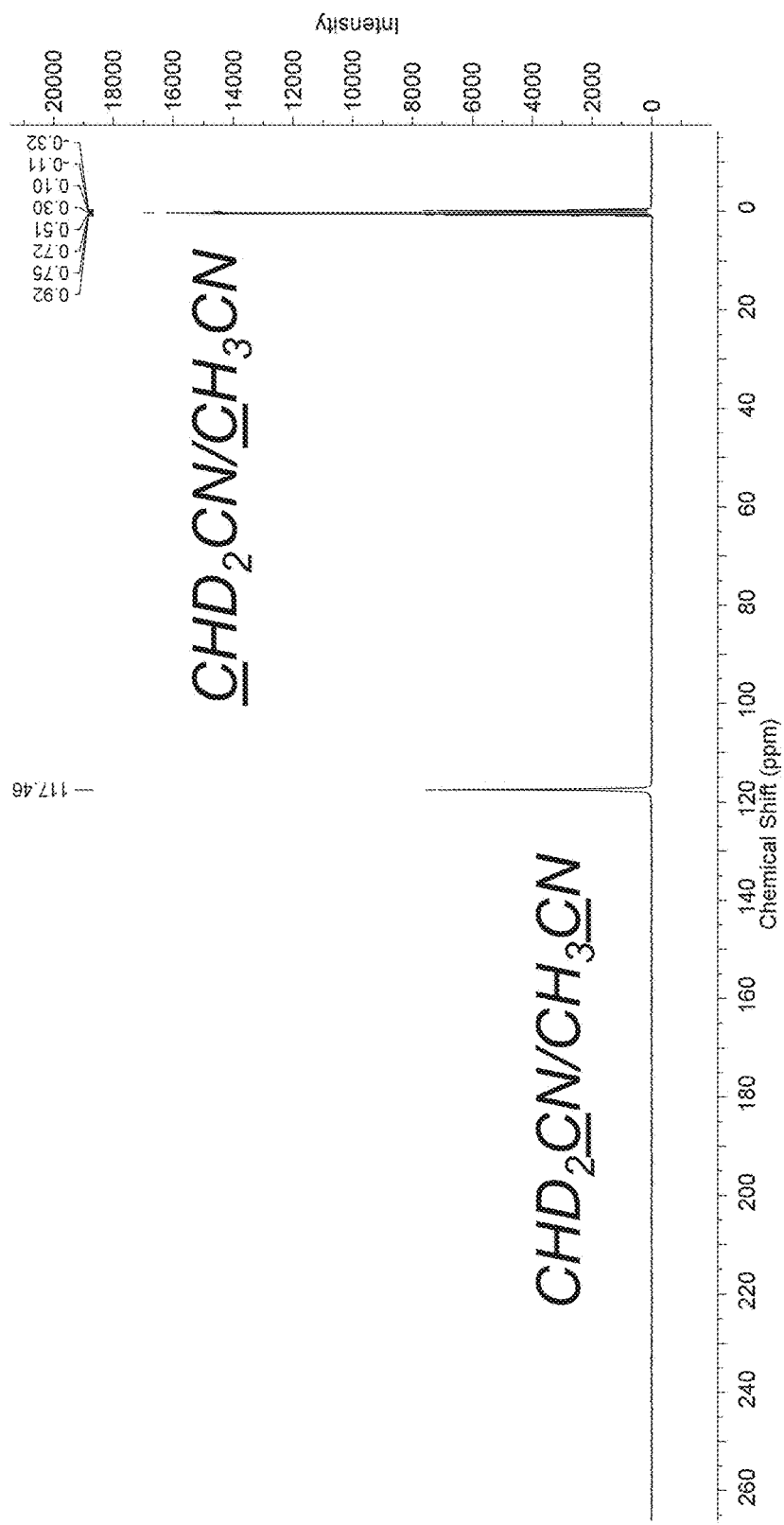
FIG. 3 is a $^{13}C$ NMR spectrum of a salt of the present invention.
Figure 4:
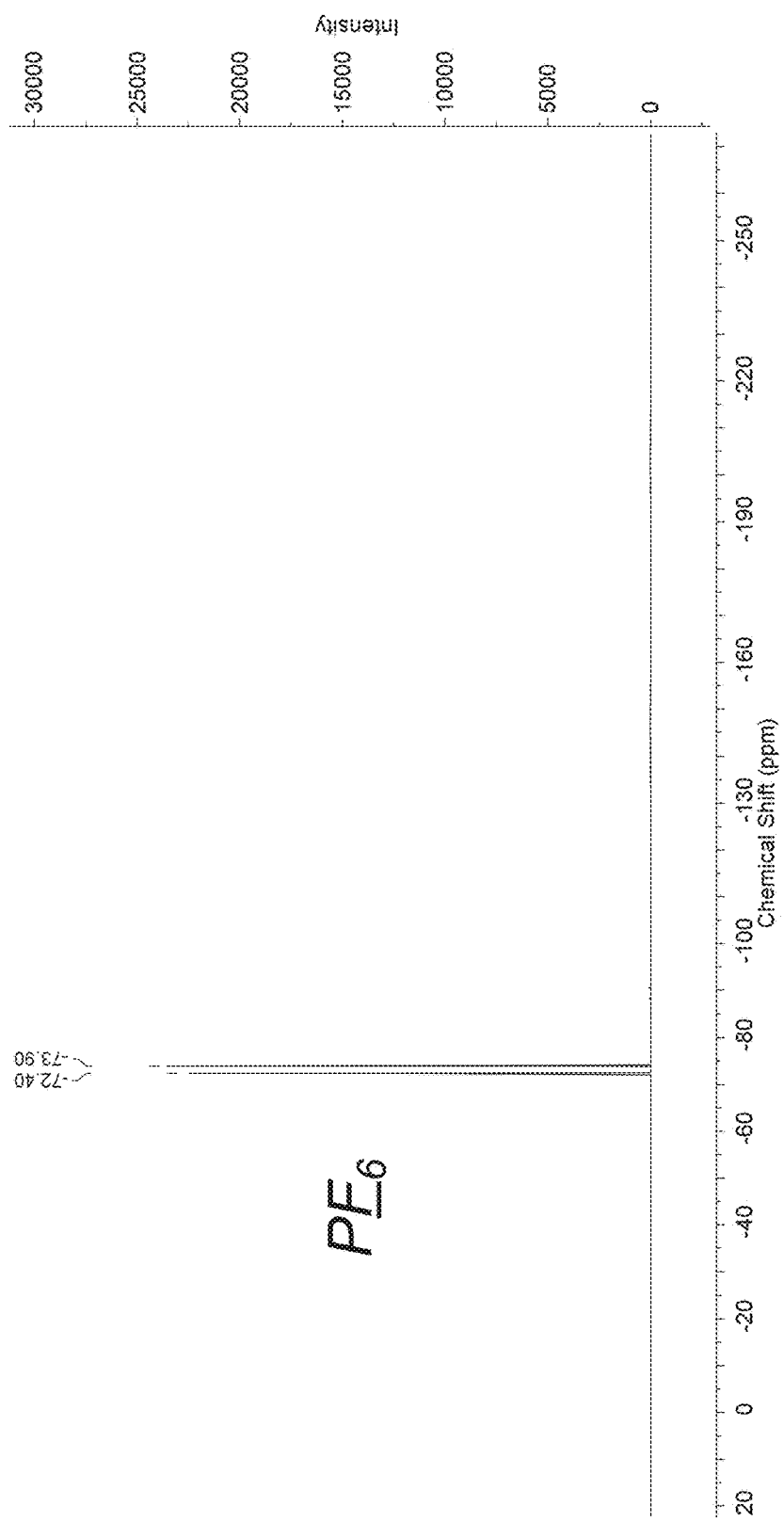
FIG. 4 is a $^{19}F$ NMR spectrum of a salt of the present invention.
Figure 5:
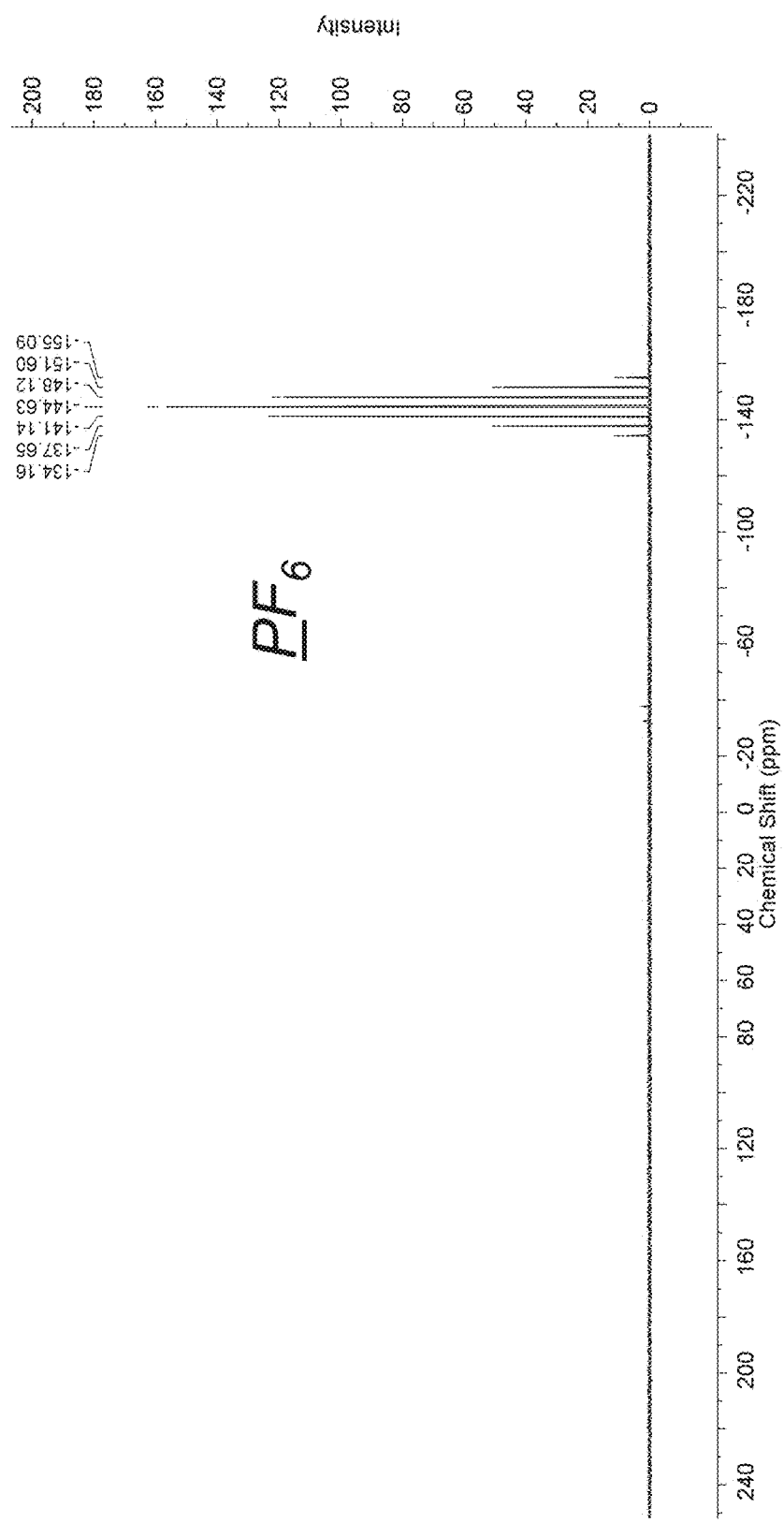
FIG. 5 is a $^{31}P$ NMR spectrum of a salt of the present invention.

A single crystal obtained from the diffusion of $Et_2O$ in to a $CH_3CN$ solution of $Mg(CH_3CN)_6(PF_6)_2$. X-ray analysis was carried out on data collected with a Bruker D8 Quest CCD diffractometer and confirmed the complex to be the desired salt (FIG. 1).

The $^1H$, $^{13}C$, $^{19}F$ and $^{31}P$ NMR spectra of the white crystalline powder of $Mg(CH_3CN)_6(PF_6)_2$ are shown in FIGS. 2 to 5, respectively. Notably, the $^{19}F$ and $^{31}P$ NMR spectra exhibited a doublet and heptet, respectively, characteristic of the $PF_6^-$ anion. NMR spectra were recorded at 298.0 K on a Bruker 500 MHz AVIII HD Smart Probe Spectrometer ($^1H$ at 500 MHz, $^{31}P$ 202 MHz, $^{13}C$ 125 MHz, $^{19}F$ 471 MHz) or a Bruker 400 MHz AVIII HD Smart Probe spectrometer ($^1H$ at 400 MHz, $^{31}P$ 162 MHz, $^{13}C$ 101 MHz, $^{19}F$ 376 MHz) unless otherwise specified. Chemical shifts ($\delta$, ppm) are given relative to residual solvent signals for $^1$H and $^{13}$C, to external 85% $H_3PO_4$ for $^{31}$P and to $CCl_3F$ for $^{19}$F.

Bulk purity of $Mg(CH_3CN)_6(PF_6)_2$ was confirmed by elemental analysis (C, H, and N). Elemental microanalytical data were obtained from the University of Cambridge, Department of Chemistry microanalytical service. Additionally, the IR spectrum of 1 exhibits the expected C≡N stretching band at 2299 cm$^{-1}$. FT-IR spectroscopic measurements were conducted using a PerkinElmer universal ATR sampling accessory.

EXAMPLE 3

Use of $Mg(CH_3CN)_6(PF_6)_2$ as an Electrolyte Salt

All Cyclic voltammetry and linear sweep voltammetry experiments reported below were performed in a glovebox (MBraun) under an atmosphere of dry argon using dry solvents. Cyclic voltammetry and linear sweep voltammetry were performed using an IVIUM CompactStat.

Figure 6:
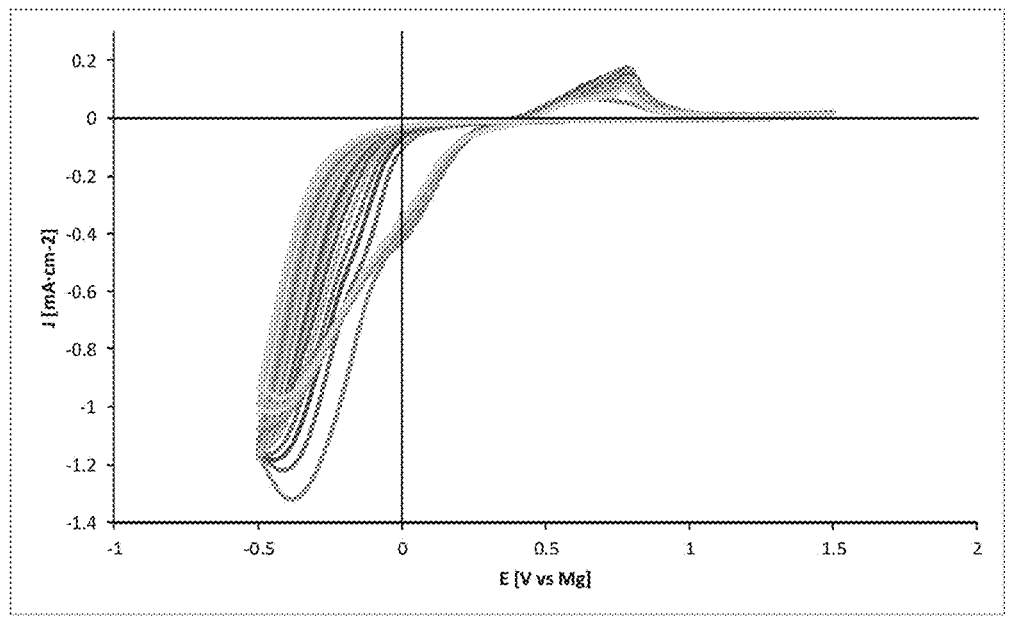
FIG. 6 is a cyclic voltammogram of a 0.12 M solution of $Mg(CH_3CN)_6(PF_6)_2$ in 1:1 THF—$CH_3CN$ cycling at a rate of 25 mVs$^{-1}$ in a three electrode cell containing a glassy carbon working electrode and Mg reference and counter electrodes at 25° C.

FIG. 6 shows the cyclic voltammetry of a 0.12 M solution of $Mg(CH_3CN)_6(PF_6)_2$ in a 1:1 ratio with THF—$CH_3CN$. The electrolyte was cycled reversibly between −0.5 and 1.5 V vs Mg over at least 20 cycles at a rate of 25 mVs$^{-1}$ using a glassy carbon working electrode (purchased from Alvatek Limited) and an Mg reference and counter electrodes (Magnesium ribbon from Sigma Aldrich (99.9%)). The electrolyte could be cycled for at least 20 cycles with only moderate loss in plating/stripping current, exhibiting a small stripping overpotential (ca. 0.25 V vs Mg) and a plating onset at 0 V vs Mg/Mg$^{2+}$. Broad features observed around 0 V vs Mg/Mg$^{2+}$ returning to positive potentials are thought to be the result of capacitive effects arising from the high surface area glassy carbon electrode.

Figure 7:
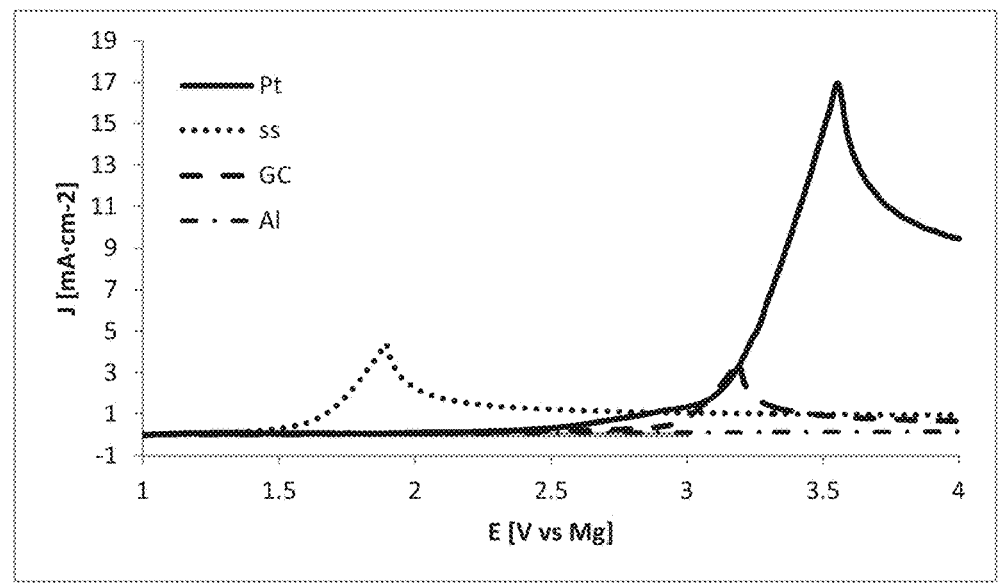
FIG. 7 is a linear sweep voltammogram of 0.12 M $Mg(CH_3CN)_6(PF_6)_2$ in 1:1 THF—$CH_3CN$ scanning at a rate of 25 mVs$^{-1}$ on platinum, stainless steel, glassy carbon, and aluminium working electrodes.

The electrochemical stability of the optimized $Mg(PF_6)_2$ electrolyte was further studies by performing linear sweep voltammetry (LSV) using platinum (Pt) (Platinum wire (99.95%) purchased from Alfa Aesar), glassy carbon (GC), stainless steel (ss) (Stainless steel 316 purchased from Advent Research materials), and aluminium (Al) working electrodes (Purchased from Dexmet corp.) (results shown in FIG. 7). On the Pt and GC electrodes the onset of electrolyte oxidation occurs around 3 V vs Mg/Mg$^{2+}$ while on ss oxidation occurs at potentials around 1.5 V vs Mg/Mg$^{2+}$. Virtually no current is observed when scanning with the Al working electrode out to 4 V vs Mg/Mg$^{2+}$, suggesting that the Al surface is passivated. The 1:1 THF—$CH_3CN$ electrolyte solvent mixture was found to exhibit superior electrochemical stability and plating-stripping reversibility on GC than the 0.12 M electrolyte solution in pure $CH_3CN$ under the same conditions.

EXAMPLE 4

Use of $Mg(CH_3CN)_6(PF_6)_2$ as an Electrolyte in an Mg-ion Cell

Figure 8:
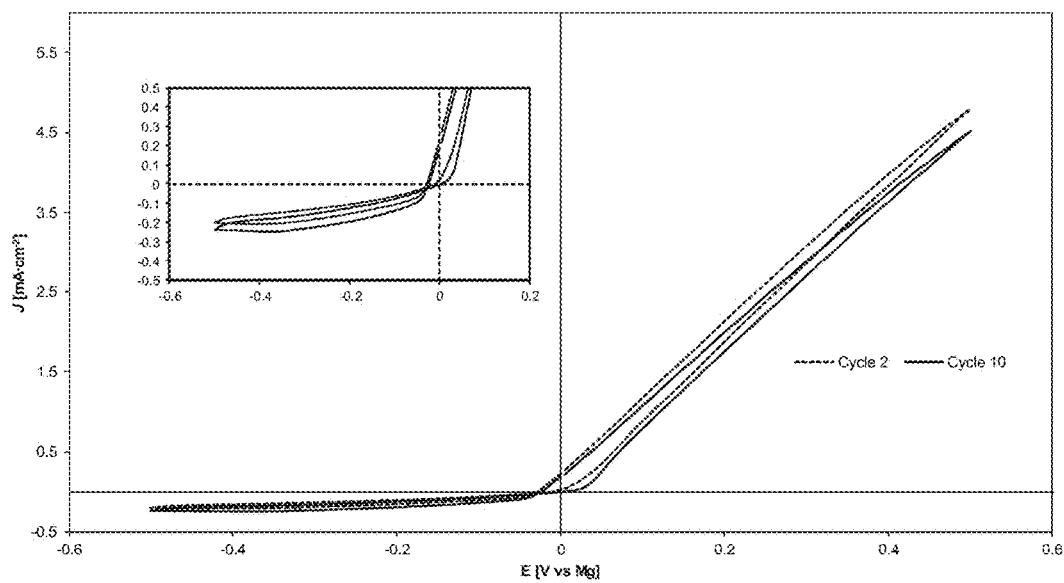
FIG. 8 is a cyclic voltammogram of 0.12 M solution of $Mg(CH_3CN)_6(PF_6)_2$ in 1:1 THF—$CH_3CN$ cycling at a rate of 50 mVs$^{-1}$ in a symmetric three electrode Mg|Mg|Mg flooded cell at 25° C. (insets: expansion of the region showing Mg plating)
Figure 9:
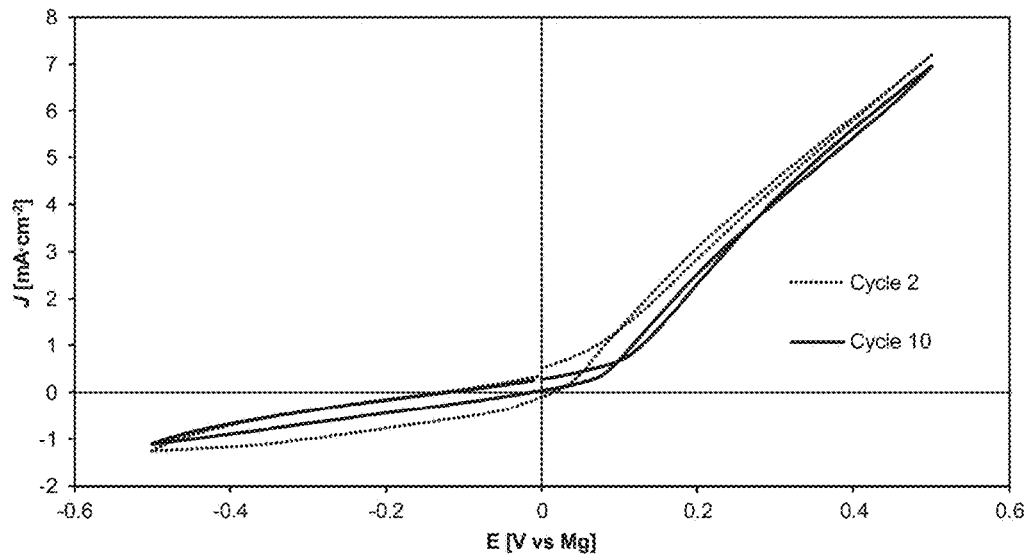
FIG. 9 is a cyclic voltammogram of 0.71 M solution of $Mg(CH_3CN)_6(PF_6)_2$ in 1:1 THF—$CH_3CN$ cycling at a rate of 50 mVs$^{-1}$ in a symmetric three electrode Mg|Mg|Mg flooded cell at 25° C.

A study was conducted into the use of the $Mg(CH_3CN)_6(PF_6)_2$ salt as an electrolyte in a symmetrical cell (Mg|Mg|Mg) using Mg as the working electrode. Battery cycling was conducted on an Arbin BT2043 battery test system. Both the 0.12 and 0.71 M solutions of $Mg(CH_3CN)_6(PF_6)_2$ in 1:1 ratio with THF—$CH_3CN$ were cycled between −0.5 and 0.5 V vs. Mg at a rate of 50 mV·s$^{-1}$ for 10 cycles. FIGS. 8 and 9 show the voltammograms of the 0.12 and 0.71 M electrolyte solutions. These solutions have exhibited reversible plating and stripping of Mg over 10 cycles with little to no loss in plating current density. The reversibility of these processes, showing virtually no attenuation of current density, suggests that the Mg electrode remains free of insulating or passivating films.

Figure 10:
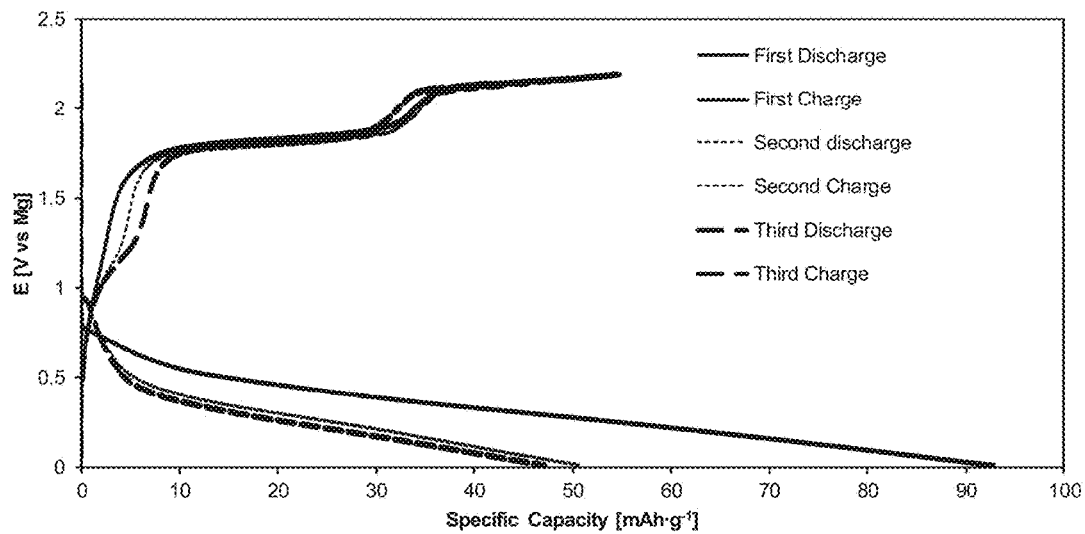
FIG. 10 shows three galvanostatic discharge-charge cycles of a coin cell containing a 0.71 M solution of $Mg(CH_3CN)_6(PF_6)_2$ in 1:1 THF—$CH_3CN$, an Mg anode, an $Mo_3S_4$ cathode, and Al current collectors, cycling at a rate of C/100.
Figure 11:
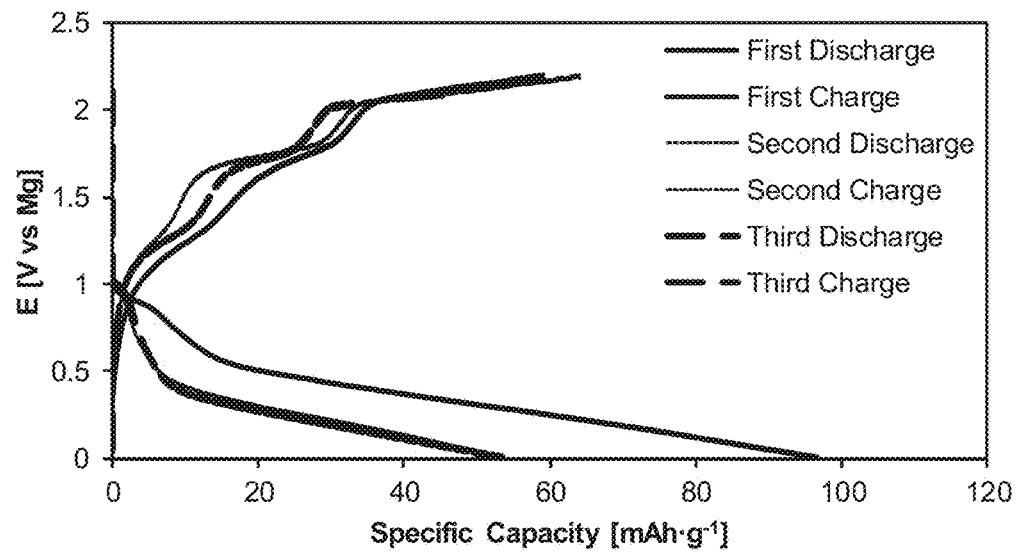
FIG. 11 shows three galvanostatic discharge-charge cycles of a coin cell containing a 0.71 M solution of $Mg(CH_3CN)_6(PF_6)_2$ in 1:1 THF—$CH_3CN$, an Mg anode, an $Mo_3S_4$ cathode, and carbon film current collectors, cycling at a rate of C/100.

From the above results, it is understood that an $Mg(PF_6)_2$ based electrolyte can facilitate the reversible plating and stripping of Mg using GC as well as Mg electrodes. A further investigation of this new electrolyte was conducted in prototype coin cell batteries. The 0.71 M electrolyte solution was used in coin cells constructed using an Mg anode and a Chevrel phase cathode ($Mo_3S_4$). Owing to the observed reactivity of this electrolyte on stainless steel, unreactive carbon film current collectors were employed to limit possible side reactions. The coin cells, cycled at C/100, showed reversible charge-discharge profiles (shown with Al current collectors and carbon film (Carbon filled polyethylene purchased from Goodfellow Cambridge Limited) current collectors in FIGS. 10 and 11, respectively). These cells could be cycled for at least three cycles reaching a maximum reversible capacity of 51 and 53 mAhg$^{-1}$ for the Al and carbon film cells, respectively, while suffering a moderate fade in capacity. It is understood that this observed fade is common for many Mg-ion systems.

The invention claimed is:

1. A salt of the general formula:

$$Mg^{2+}(L)_x(PF_6)_2 \qquad (i)$$

wherein x represents a number between 1 and 6; and
each L represents a ligand selected from one of the following compounds:
a halomethane,
a cyclic crown ether; or
a nitrile of the general formula R—C≡N.

2. The salt of claim 1, wherein x is greater than 1, and L represents a ligand selected from only one of the following compounds:
a halomethane,
a cyclic crown ether; or
a nitrile of the general formula R—C≡N.

3. The salt of claim 2, wherein each ligand L is acetonitrile.

4. The salt of claim 1, wherein x is equal to 6, ligand L is a nitrile and R represents an organic group independently selected from the following: methyl, ethyl, propyl, butyl, $^t$butyl, pentyl, ethylene, propylene, butylene, pentylene, toluene, naphthalene, or phenyl.

5. The salt of claim 4, wherein R is the same for each ligand represented by L.

6. The salt of claim 1, wherein x is equal to 1 and L is a cyclic crown ether selected from one of the following: [12]-crown-4, [18]-crown-6, [24]-crown-8.

7. The salt of claim 1, wherein the halomethane is dichloromethane.

8. An electrolyte comprising the salt of claim 1.

9. A cell comprising the electrolyte of claim 8.

10. The cell of claim 9, wherein the cell is a magnesium cell or a magnesium-ion cell.

11. A battery comprising the electrolyte of claim 8.

12. The battery of claim 11, wherein the battery is a magnesium battery or a magnesium-ion battery.

13. A method of making a salt of the general formula:

$$Mg^{2+}(L_y)_x(PF_6)_2 \qquad (i)$$

wherein x represent a number between 1 and 6,
$L_y$ represents a ligand independently selected from any one of the following compounds:
- a halomethane,
- a cyclic crown ether; or
- a nitrile of the general formula R—C≡N; and $L_y$ comprises a mixture of compounds $L_1$ and $L_2$; the method comprising:
providing Mg metal,
washing and activating the Mg metal in a first dry solution comprising a first compound ($L_1$),
treating the solution of activated Mg metal and first compound $L_1$ with $NOPF_6$ in a second dry solution comprising a second compound ($L_2$),
removing the residual solvent, and
recrystallizing the remaining solid to form the salt of Formula (i).

14. The method of claim 13, wherein x is greater than 1, and $L_y$ represents a ligand selected from only one of the following compounds:
- a halomethane,
- a cyclic crown ether; or
- a nitrile of the general formula R—C≡N.

15. The method of claim 13, wherein x is equal to 6, $L_1$ and $L_2$ are each nitriles, and for $L_1$ and $L_2$ R independently represents an organic group selected from the following: methyl, ethyl, propyl, butyl, ʹbutyl, pentyl, ethylene, propylene, butylene, pentylene, toluene, naphthalene, or phenyl.

16. The method of claim 15, wherein $L_1$ and $L_2$ are the same nitrile.

17. The method of claim 16, wherein $L_1$ and $L_2$ are both acetonitrile.

18. The method of claim 13, wherein x is equal to 1 and $L_y$ is a cyclic crown ether selected from one of the following: [12]-crown-4, [18]-crown-6, [24]-crown-8.

19. The method of claim 13, wherein the halomethane is dichloromethane.

* * * * *